US011435364B2

(12) United States Patent
Zager et al.

(10) Patent No.: US 11,435,364 B2
(45) Date of Patent: Sep. 6, 2022

(54) METHODS OF TREATING PATIENTS AT RISK FOR RENAL INJURY AND RENAL FAILURE

(71) Applicant: RENIBUS THERAPEUTICS, INC., Lantana, TX (US)

(72) Inventors: Richard A. Zager, Mercer Island, WA (US); Donald Jeffrey Keyser, Southlake, TX (US); Alvaro F. Guillem, Lantana, TX (US)

(73) Assignee: RENIBUS THERAPEUTICS, INC., Southlake, TX (US)

( * ) Notice: Subject to any disclaimer, the term of this patent is extended or adjusted under 35 U.S.C. 154(b) by 0 days.

(21) Appl. No.: 16/422,156

(22) Filed: May 24, 2019

(65) Prior Publication Data
US 2020/0057076 A1 Feb. 20, 2020

Related U.S. Application Data

(60) Provisional application No. 62/676,157, filed on May 24, 2018, provisional application No. 62/715,508, filed on Aug. 7, 2018.

(51) Int. Cl.
| | | |
|---|---|---|
| *G01N 33/68* | (2006.01) | |
| *A61K 31/277* | (2006.01) | |
| *A61K 31/409* | (2006.01) | |
| *A61K 33/26* | (2006.01) | |

(52) U.S. Cl.
CPC ....... *G01N 33/6893* (2013.01); *A61K 31/277* (2013.01); *A61K 31/409* (2013.01); *A61K 33/26* (2013.01); *G01N 2800/347* (2013.01)

(58) Field of Classification Search
CPC .... A61K 33/26; A61K 31/409; A61K 31/277; G01N 2800/347; G01N 2800/50; G01N 2800/54; G01N 33/6875
See application file for complete search history.

(56) References Cited

U.S. PATENT DOCUMENTS

| | | | | |
|---|---|---|---|---|
| 2013/0324599 A1* | 12/2013 | Anderson | ............... | A61P 19/02 514/510 |
| 2016/0228394 A1* | 8/2016 | Forbes | ................... | A61K 47/55 |
| 2017/0112869 A1* | 4/2017 | Zager | ...................... | A61P 37/06 |
| 2017/0290863 A1* | 10/2017 | Ichim | ................... | C12N 5/0682 |

FOREIGN PATENT DOCUMENTS

| | | |
|---|---|---|
| WO | 2014113558 A1 | 7/2014 |
| WO | WO 2014113558 A1 * | 7/2014 |

OTHER PUBLICATIONS

Pena et al. ("Biomarkers Predicting Outcome in Patients with Advanced Renal Cell Carcinoma: Results from Sorafenib Phase III Treatment Approaches in Renal Cancer Global Evaluation Trial," in American Association for cancer Research, Jul. 22, 2010).*

(Continued)

*Primary Examiner* — Blessing M Fubara

(74) *Attorney, Agent, or Firm* — Culhane Meadows, PLLC; Jeff B. Vockrodt

(57) ABSTRACT

The p21 biomarker is utilized in the evaluation of whether a patient is suffering from kidney injury or failure, and can be used in methods of treating kidney injury or failure by determining the appropriateness of one or more of initiating renal replacement therapy, withdrawing delivery of compounds that are known to be damaging to the kidney, delaying or avoiding procedures that are known to be damaging to the kidney, and modifying diuretic administration.

13 Claims, 8 Drawing Sheets

Specification includes a Sequence Listing.

(56) References Cited

OTHER PUBLICATIONS

Vijayan et al., ("Clinical Use of the URIN Biomaker [TIMP-2] X [IGFBP7] for acute Kidney Injury Risk Assessment," in Americ Journal of Kidney disease 2016, vol. 8, No. 1, 19-28).*
Kivinen et al., "Ras induces p21 Cip1/Waf1 cyclin kinase inhibitor transcriptionally through Sp1-binding Sites" in Oncogen 1999 18, 6252-6261; https://www.nature.com/articles/1203000.pdf (Year: 1999).*
J.L. Bos, "p21ras: An Oncoprotein Functioning in Growth Factor-induced Signal Transduction" in European Journal of Cancer, vol. 31A, pp. 1051-1054, 1995 (Year: 1995).*
Price et al., "The cell cycle and acute kidney injury," Kidney International, vol. 76, 2009, pp. 604-613.
He et al., "Inhibition of SIRT2 Alleviates Fibroblast Activation and Renal Tubulointerstitial Fibrosis via MDM2," Cellular Physiology and Biochemistry, vol. 46, 2018, pp. 451-460.
Johnson et al., "Mechanisms and consequences of oxidant-induced renal preconditioning: an Nrf2-dependent, P21-independent, anti-senescence pathway," Nephrol Dial Transplant, vol. 33, 2018, pp. 1927-1941.
Andrade et al., "Acute Kidney Injury as a Condition of Renal Senescence," Cell Transplantation, vol. 27(5), 2018, pp. 739-753.
International Search Report and Written Opinion issued in PCT/US2019/034018, dated Nov. 5, 2019.

\* cited by examiner

SEQUENCE LISTING

```
<160> NUMBER OF SEQ ID NOS: 1

<210> SEQ ID NO 1
<211> LENGTH: 164
<212> TYPE: PRT
<213> ORGANISM: Human

<400> SEQUENCE: 1

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

METHODS OF TREATING PATIENTS AT RISK FOR RENAL INJURY AND RENAL FAILURE

RELATED APPLICATIONS

The present application claims benefit from U.S. Provisional Patent Application Ser. Nos. 62/676,157 filed May 24, 2018, and 62/715,508 filed Aug. 7, 2018, each of which are incorporated by reference herein in their entirety.

BACKGROUND OF THE INVENTION

The kidney is responsible for water and solute excretion from the body. Its functions include maintenance of acid-base balance, regulation of electrolyte concentrations, control of blood volume, and regulation of blood pressure. Kidneys also help maintain blood hemoglobin/hematocrit by producing erythropoietin and also produce activated vitamin D. As such, loss of kidney function through injury and/or disease results in substantial morbidity and mortality. A detailed discussion of renal injuries is provided in Harrison's Principles of Internal Medicine, 17.sup.th Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 15-30% of cardiopulmonary bypass surgeries, and up to 35% of intensive care admissions. ARF may be categorized as prerenal, intrinsic renal, or post-renal in causation. Intrinsic renal disease can be further divided into glomerular, tubular, interstitial, and vascular abnormalities. Major causes of ARF are described in the following table, which is adapted from the Merck Manual, 17.sup.th ed., Chapter 222, and which is hereby incorporated by reference in their entirety:

There is interest in developing methods for early diagnosis and prognosis of renal injury and renal failure that would make timely intervention to prevent progression to chronic kidney damage. One such test relies on biomarkers TIMP-2 (tissue inhibitor of metalloproteinases 2) and IGFBP-7 (insulin-like growth factor-binding protein 7), and is marketed as NEPHROCHECK®® by Astute Medical of San Diego, Calif. The patents include, for example, U.S. Pat. No. 8,778,615, entitled "Methods and compositions for diagnosis and prognosis of renal injury and renal failure," issued to Joseph Anderberg et al. and assigned to Astute Medical, Inc. The '615 patent discloses diagnosis of kidney injury and kidney failure using a combination of several biomarkers. Other related patents include U.S. Pat. Nos. 9,879,091; 9,822,172; 9,784,750; 9,733,261; 9,696,322; 9,470,695; 9,459,261; 9,417,250; 9,366,683; 9,360,488; 9,229,010; 9,057,735; 9,029,093; 8,993,250; and 8,871,459.

The Astute Medical NEPHROCHECK®® Test System is intended to be used in conjunction with clinical evaluation in patients who currently have or have had within the past 24 hours acute cardiovascular and or respiratory compromise and are ICU patients as an aid in the risk assessment for moderate or severe acute kidney injury (AKI) within 12 hours of patient assessment. The NEPHROCHECK®® Test System is intended to be used in patients 21 years of age or older. The FDA has approved NEPHROCHECK®® for detection of "renal stress."

One problem with TIMP-2 and IGFBP-7 as biomarkers for kidney stress or kidney injury is that they are not made in the kidney in response to injury. Rather, their elevation in urine reflects a failure to reabsorb these proteins following their filtration from plasma, and from their loss from kidney tubule cells. Furthermore, their utility has not been demonstrated to be superior to urinary albumin, long recognized standard for measuring kidney damage. While the NEPHROCHECK® test has been proposed as a cell cycle arrest test, this is unlikely to be accurate, because the NEPHROCHECK® markers are lost from the kidney, making it highly unlikely that they could trigger the cell cycle arrest/senescence process. Because these processes cause progressive kidney (as well as other organ) damage, it is critical to develop markers of these processes that will allow physicians to introduce new therapies.

Still a need exists to develop treatments for further kidney injury based on more stable biomarkers that are indicative of early kidney injury. In particular, there is a need to identify urinary markers of a post injury process known as "cell cycle arrest." This is a process that can lead to "premature tissue aging", known as "senescence."

SUMMARY OF THE INVENTION

The present invention relates to methods of treating patients at risk for having suffered kidney injury or kidney disease, including kidney disease progression, or have undergone a kidney transplant. The methods generally relate to (a) performing an assay to determine the level of p21 in the patient; and (b) if the patient exhibits an elevated level of p21, treating the patient to reduce the risk of further kidney injury. The treatment may include one or more of administration of one or more steroids, ACE inhibitors, NRF2 activators, Angiotensin II receptor blockers, antioxidants, aldosterone antagonists, anti-inflammatory, anti-fibrotic, vasopressin antagonists, SGLT-2 inhibitors, immunosuppressive agents, organ protection, or acute kidney injury treatments, initiating renal replacement therapy, withdrawing delivery of compounds that are known to be damaging to the kidney, delaying or avoiding procedures that are known to be damaging to the kidney, and modifying diuretic administration. In certain cases the treatment may include administration of one or more steroids, cellular senescence blocking agents, ACE inhibitors, NRF2 activators, angiotensin II receptor blockers, anti-inflammatory, anti-fibrotic, vasopressin antagonists, SGLT-2 inhibitors, immunosuppressive agents, organ protection, or acute kidney injury treatments.

In one aspect, a patient may be treated with a combination of iron or an iron complex (e.g., iron sucrose), and a heme protein degradation inhibitor (tin protoporphyrin, SnPP). In another aspect, the patient may be treated with a circuminoid formulation. In yet another aspect, the patient may be treated with bardoxolone methyl.

In one aspect, the step (a) of performing an assay to determine the level of p21 in the patient, also comprises performing an assay to determine the level of microalbumin, ferritin, hemopexin, and haptoglobin in the patient.

In one embodiment, the invention may include a method of determining the risk of progression of acute or chronic kidney disease and tissue senescence comprising: (a) performing an assay to determine the level of organ senescence as shown by the level of serum, urine, or plasma p21 levels in the patient; and (b) if the patient exhibits an elevated level of p21, administer a dosage of a drug known to treat senescence in the patient. In certain embodiments, the dosage of the drug known to treat senescence is increased upon determination that the level of p21 is increased.

In one embodiment, the invention may include a method of treating a patient determined to be at risk for future kidney injury comprising: (a) performing an assay to determine the level of p21 in the patient; (b) performing an assay to determine the level of urinary albumin in the patient; and (c) if the patient exhibits elevated levels of p21 and albumin, treating the patient to reduce the risk of further kidney injury, wherein the treatment comprises one or more of administration of one or more steroids, ACE inhibitors, NRF2 activators, antioxidants, aldosterone antagonists, anti-inflammatory, anti-fibrotic, vasopressin antagonists, SGLT-2 inhibitors, immunosuppressive agents, organ protection, or acute kidney injury treatments, initiating renal replacement therapy, withdrawing delivery of compounds that are known to be damaging to the kidney, delaying or avoiding procedures that are known to be damaging to the kidney, and modifying diuretic administration.

In one aspect, a patient may be treated with a combination of iron or an iron complex (e.g., iron sucrose), and a heme protein degradation inhibitor (tin protoporphyrin, SnPP). In another aspect, the patient may be treated with a circuminoid formulation.

In yet another aspect, the patient may be treated with bardoxolone methyl. In one aspect, the step (a) of performing an assay to determine the level of p21 in the patient, also comprises performing an assay to determine the level of microalbumin, ferritin, hemopexin, and haptoglobin in the patient.

In one embodiment, the invention may include a method for evaluating renal status in a subject, comprising: (a) performing one or more assays configured to detect a kidney injury marker including measuring p21 present in a body fluid sample obtained from the subject, (b) correlating the measured p21 level to a likelihood that the subject is at risk of a future acute renal injury within 72 hours of the time at which the body fluid sample is obtained from the subject by using the assay result to assign the subject to a predetermined subpopulation of individuals having a known predisposition of a future acute renal injury within 72 hours; and (c) treating the subject based on the predetermined subpopulation of individuals to which the patient is assigned, wherein the treatment comprises one or more of administration of one or more steroids, ACE inhibitors, NRF2 activators, antioxidants, aldosterone antagonists, anti-inflammatory, anti-fibrotic, vasopressin antagonists, SGLT-2 inhibitors, immunosuppressive agents, organ protection, or acute kidney injury treatments, initiating renal replacement therapy, withdrawing delivery of compounds that are known to be damaging to the kidney, delaying or avoiding procedures that are known to be damaging to the kidney, and modifying diuretic administration. In one aspect, a patient may be treated with a combination of iron or an iron complex (e.g., iron sucrose), and a heme protein degradation inhibitor (tin protoporphyrin, SnPP). In another aspect, the patient may be treated with a circuminoid (e.g., tetrahydrocurcumin) formulation. In yet another aspect, the patient may be treated with bardoxolone methyl.

In one embodiment, the invention may include a method of treating a patient at risk for having suffered kidney injury or kidney disease progression comprising: (a) performing an assay to determine the level of p16ink4a, p19, and p21 in the patient; (b) determining by considering the relative levels of p16ink4a, p19, and p21 whether the patient is suffering from kidney injury or kidney disease; and (c) if the patient is determined to be suffering from kidney injury or kidney disease, treating the patient to reduce the risk of further kidney injury, wherein the treatment comprises one or more of administration of one or more steroids, ACE inhibitors, NRF2 activators, antioxidants, aldosterone antagonists, anti-inflammatory, anti-fibrotic, vasopressin antagonists, SGLT-2 inhibitors, immunosuppressive agents, organ protection, or acute kidney injury treatments, initiating renal replacement therapy, withdrawing delivery of compounds that are known to be damaging to the kidney, delaying or avoiding procedures that are known to be damaging to the kidney, and modifying diuretic administration. The patient may be a patient who has undergone a kidney transplant.

In one aspect, a patient may be treated with a combination of iron or an iron complex (e.g., iron sucrose), and a heme protein degradation inhibitor (tin protoporphyrin, SnPP). In another aspect, the patient may be treated with a circuminoid (e.g., tetrahydrocurcumin) formulation. In yet another aspect, the patient may be treated with bardoxolone methyl.

In one aspect, the step (a) of performing an assay to determine the level of p21 in the patient, also comprises performing an assay to determine the level of microalbumin, ferritin, hemopexin, and haptoglobin in the patient.

In one embodiment, the invention may include a method of treating a patient comprising: (a) performing an assay to determine the level of p16ink4a, p19, and p21 in the patient; (b) determining by considering the relative levels of p16ink4a, p19, and p21 whether the patient is suffering liver, kidney, heart or brain dysfunction, injury or senescence.

In any of the assay steps, the assay may include (i) obtaining a body fluid sample from the patient, (ii) contacting all or a portion of the body fluid sample with a binding reagent which specifically binds for detection of p21, and determining an assay result indicative of binding of the p21 to the binding reagent to provide one or more assay results.

In one embodiment, the invention may include a method of treating a patient suffering from kidney injury comprising administering an effective amount of human p21 to a patient suffering from kidney injury. The human p21 may be recombinant human p21.

In one embodiment, the invention may include a method of treating a patient suffering from kidney injury comprising administering an effective amount of human p21 activator to a patient suffering from kidney injury. The human p21 activator may include Tenovin-1.

DETAILED DESCRIPTION OF THE INVENTION

Also known as cyclin-dependent kinase inhibitor 1, or CDK-interacting protein 1, p21 is a cyclin-dependent kinase inhibitor (CKI) that is capable of inhibiting all cyclin/CDK complexes. The amino acid sequences for human p21 is as follows:

MSEPAGDVRQNPCGSKACRRLFGPVDSEQLSRDCDALMAGCIQEARERWN

FDFVTETPLEGDFAWERVRGLGLPKLYLPTGPRRGRDELGGGRRPGTSPA

LLQGTAEEDHVDLSLSCTLVPRSGEQAEGSPGGPGDSQGRKRRQTSMTDF

YHSKRRLIFSKRKP

P21 represents a major target of p53 activity and thus is associated with linking DNA damage to cell cycle arrest. This makes p21 a promising diagnostic molecule to test for this process. The present invention relates to the use of the p21 biomarker in the early detection and treatment of acute renal injury or failure, and associated cell cycle arrest, as well as testing kits for the p21 biomarker, preferably in both plasma and urine. The present inventors have found that p21 may be therapeutically used to treat conditions, particularly conditions affecting the kidney, including AKI.

Figure 1:
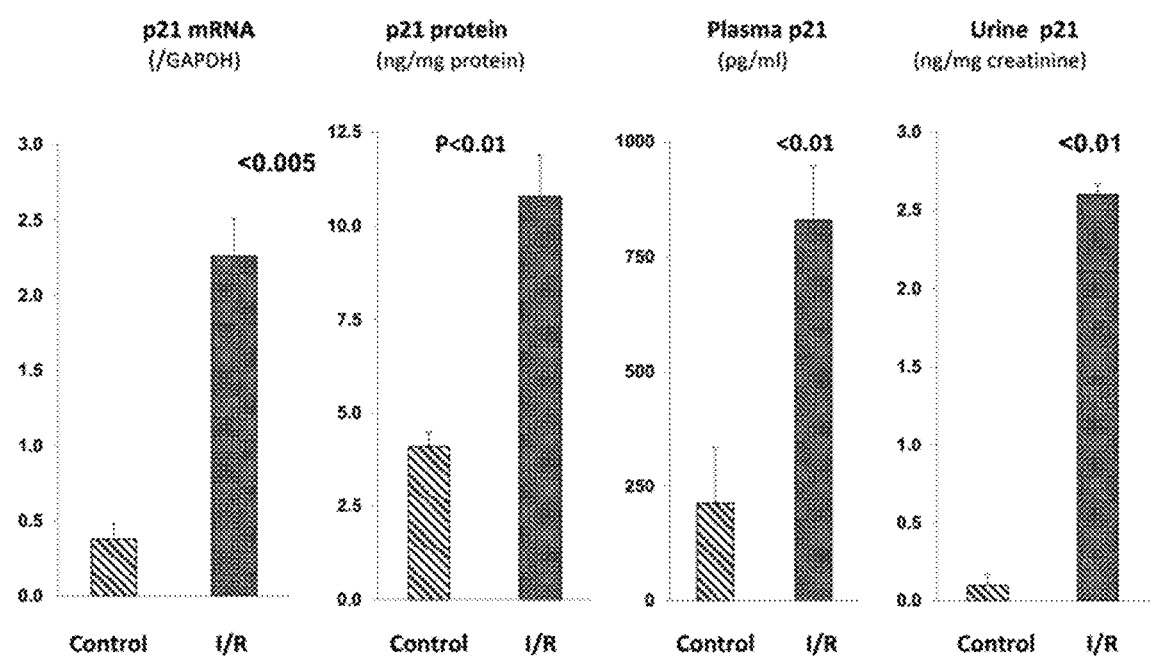
FIG. 1 shows increases in p21 elevated in several body fluids following kidney injury.

The present invention was based on the surprising discovery by the inventors that p21 is elevated in several body fluids, including urine, as early as 2 hours post injury and is sustained for at least 24 hours following ischemic injury. As shown in FIG. 1, an increase in p21 mRNA indicates increased production of p21 following kidney injury. This increase in production of p21 protein leads to increased renal cortical levels and hence increased urinary levels of p21. Some of the p21 makes it into plasma. Surprisingly, the urinary and plasma levels were unexpectedly dramatic which underscores their utility as a kidney cell injury/cell cycle arrest biomarker. That p21 a cell nuclear protein would be leaked into the urine absent cell death is quite unexpected. Without wishing to be bound by theory, the transport of p21 into urine presumptively occurs by a cellular process, exocytosis, whereby cells package protein products and then transport them out of the cell entering the urine.

The ability to detect the p21 biomarker in both the plasma and the urine makes it particularly advantageous as a biomarker for renal injury, since urine samples are routinely utilized in diagnosis of kidney conditions. The p21 biomarker can be measured using ELISA in plasma, serum and urine. Alternatively, the test can be on a test strip. In a preferred embodiment, p21 is measured using a plate that includes a first antibody that is fixed to a plate in order to capture p21. A second antibody is applied later to detect p21 captured on the plate. The detection antibody has a visible marker (e.g., horse radish peroxidase) on it that can be quantified using an ELISA plate reader. The antibody pair in one preferred aspect is Abcam #ab212072 which includes Mouse p21 Capture Antibody part #3200086 and Mouse p21 Detector Antibody part #3200087. The test strip may be used to detect p21 in blood, urine or other bodily fluids.

Figure 2:
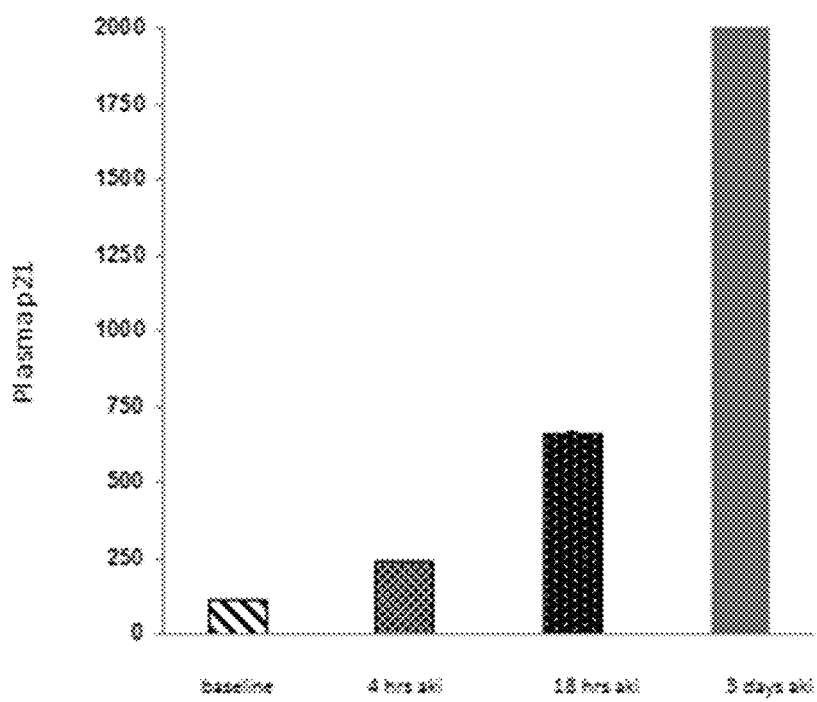
FIG. 2 shows increases in p21 over time following kidney injury.

The p21 biomarker increases with time post AKI, making a potential marker of renal disease progression due at least in part to the senescence process as shown in FIG. 2.

Figure 3:
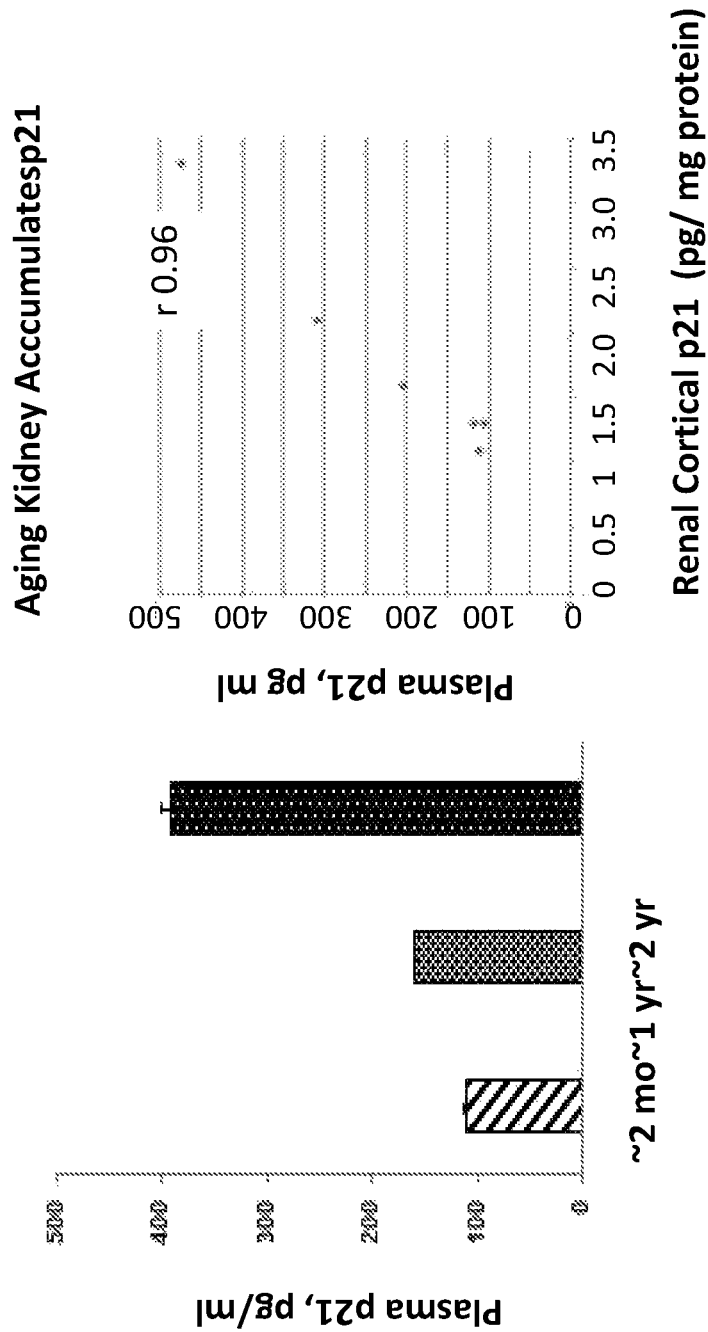
FIG. 3 shows increasing p21 with age.
Figure 4:
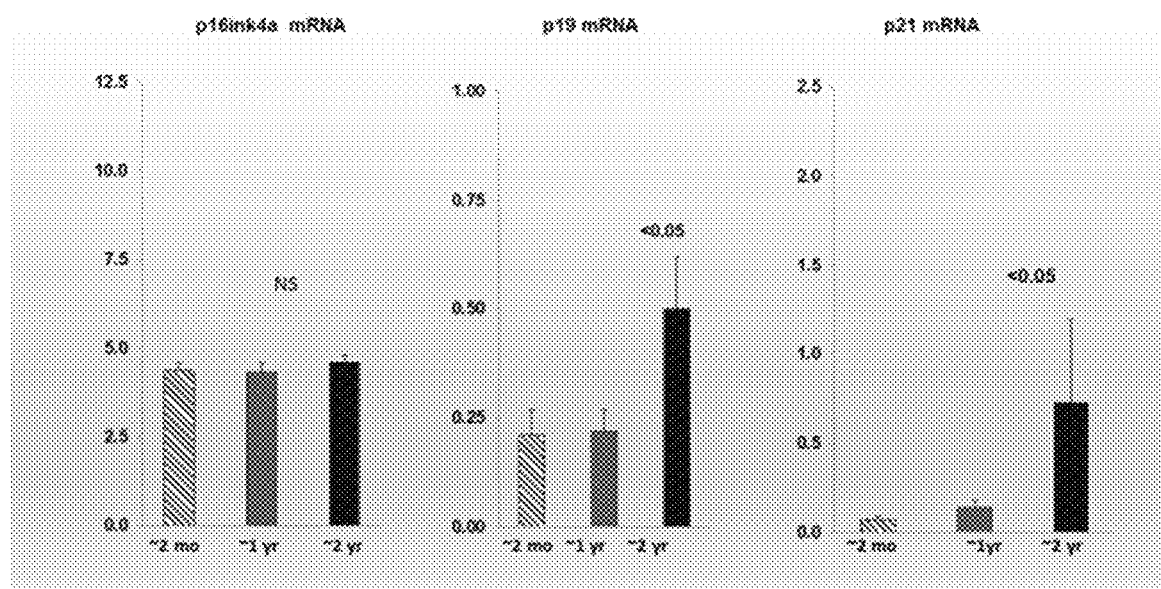
FIG. 4 shows p21 compared with liver senescence biomarkers following kidney injury.
Figure 5:
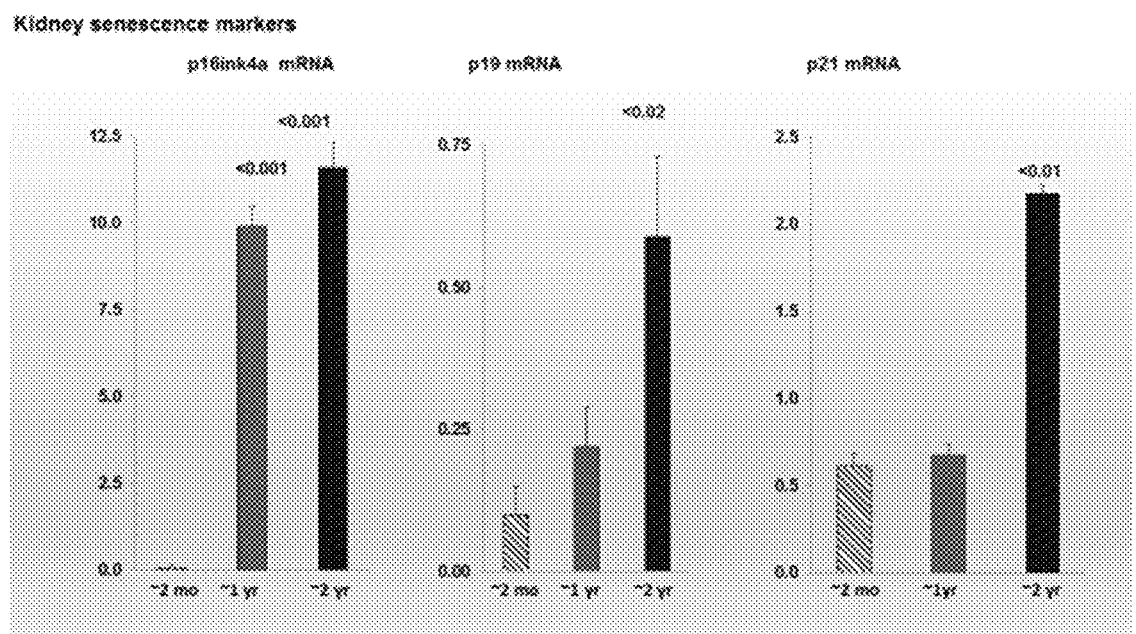
FIG. 5 shows p21 compared with kidney senescence biomarkers following kidney injury.
Figure 6:
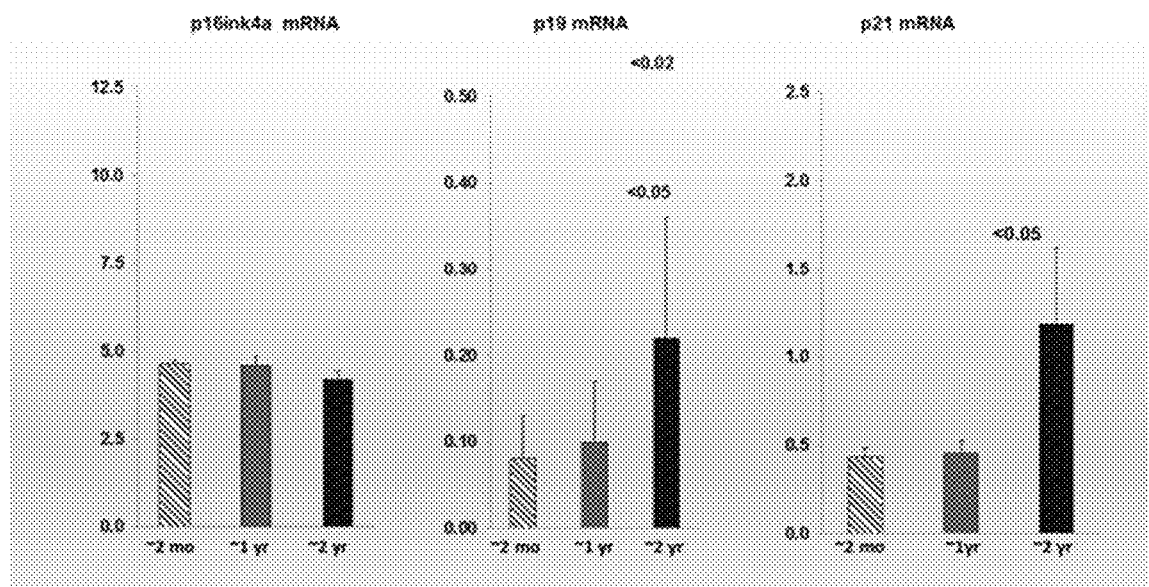
FIG. 6 shows p21 compared with heart senescence biomarkers following kidney injury.
Figure 7:
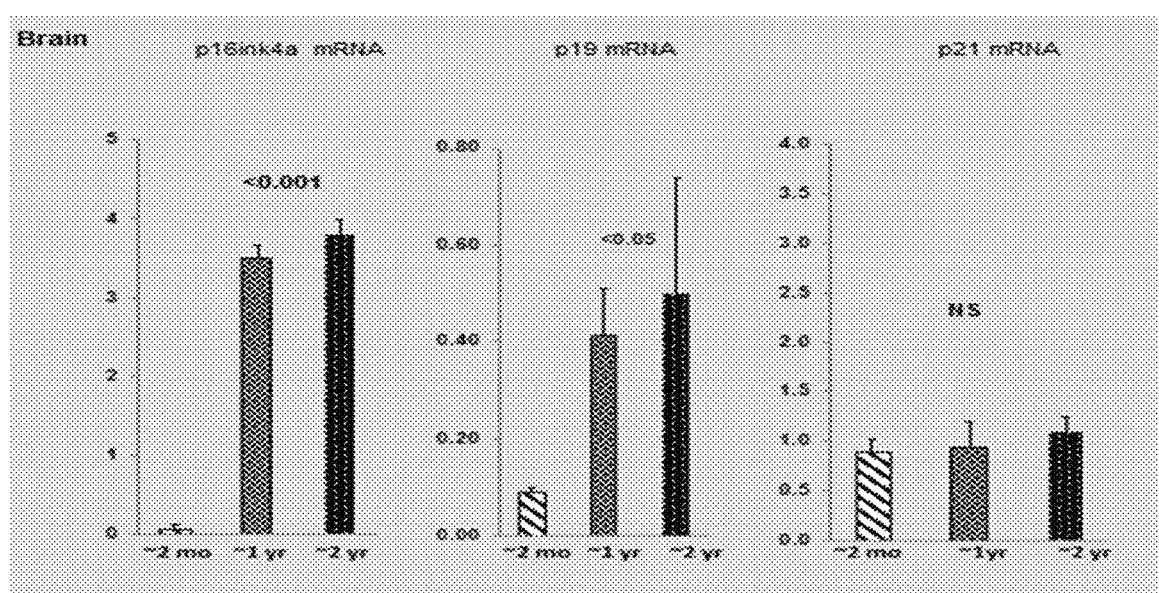
FIG. 7 shows p21 compared with brain senescence biomarkers following kidney injury.

One aspect of p21 is that the baseline level for p21 increases with age as shown in FIG. 3. These data show the level of plasma p21 increasing over time in healthy mice. The data also show that plasma p21 is tightly correlated with renal cortical p21. This information may be considered in determining whether a particular value of measured p21 is indicative of kidney injury.

The increase in p21 with age also makes the biomarker useful in detecting senescence in healthy individuals. For example, the baseline level of p21 may be utilized in determining a biological age of an individual that could differ from chronological age. All being equal, two people of the same chronological age who have greatly different levels of p21 may be seen as having a different biological age. This could be useful in assessing the ability of particular patients to tolerate more aggressive treatment options. Accordingly, one may utilize the p21 assay to determine the biological age of a patient, and utilize that information to select among treatment options for a particular patient.

The p21 biomarker may be utilized in conjunction with other biomarkers of senescence including p16 and p19 assays. The following data shows progression of these biomarkers for senescence in the brain, kidney, heart and liver of healthy mice as reflected by their mRNAs. See FIGS. 4-7 below.

In another embodiment, the invention relates to testing a patient's levels of at least three biomarkers including p16ink4a, p19, and p21, and determining based on the patent's profile for these biomarkers whether the patient is subject to liver, kidney, heart and/or brain injury or senescence. As shown in the following figures, the response of these three biomarkers varies depending upon whether injury is in the liver, kidney, heart or brain.

The invention relies on p21 as a unique marker of organ injury and its transition to cellular senescence and cell cycle arrest. At present, there are no reliable methods to make these determinations. Concomitant measurement of p16 and p19 provides supportive data for the p21 results, as they are also markers of the senescence process. Different tissues express different ratios of p21, p16 and p19 while they are undergoing senescence. Thus, the ratios of these proteins in plasma, serum or urine can help localize the senescence process to the kidney, vs. non kidney tissues (e.g., heart and brain). By so doing, these assays can provide insights into which therapeutic agents should be used for specific organ targeting.

In one aspect, the invention relates to reviewing the profile of three biomarkers to determine whether injury or senescence is related to a kidney disfunction. Because ongoing kidney injury may be difficult to determine using conventional techniques, the ability to determine whether observed p21 activity is related to kidney disfunction is particularly useful. As shown in the charts above, kidney disfunction resulting from ischemic injury shows an increase in presence of all three biomarkers whereas other organ injury results in the presence of elevated levels of less than all three biomarkers. Accordingly, an analysis of all three biomarkers can point to kidney disfunction relative generalized organ disfunction or p21 activity related to other organ injury.

In one aspect, the combination of biomarkers used to diagnose a patient with kidney injury includes an assay to determine the level of p21 in the patient, as well as assays to determine the level of microalbumin, ferritin, hemopexin, and haptoglobin in the patient.

Upon detection of kidney injury, the patient may be treated to reduce the risk of further kidney injury. The treatment may include one or more of administration of one or more steroids, ACE inhibitors, NRF2 activators, antioxidants, aldosterone antagonists, Angiotensin II receptor blockers (ARBs), anti-inflammatory, anti-fibrotic, vasopressin antagonists, SGLT-2 inhibitors, immunosuppressive agents, organ protection, or acute kidney injury treatments, initiating renal replacement therapy, withdrawing delivery of compounds that are known to be damaging to the kidney, delaying or avoiding procedures that are known to be damaging to the kidney, and modifying diuretic administration.

Suitable steroids may include methylprednisolone and prednisolone. Suitable ACE inhibitors include benazepril (Lotensin), captopril (Capoten-discontinued brand), enalapril (Vasotec, Epaned), fosinopril (Monopril-Discontinued brand), lisinopril (Prinivil, Zestril, Qbrelis), moexipril (Univasc-Discontinued brand), perindopril (Aceon), quinapril (Accupril), ramipril (Altace), trandolapril (Mavik). Suitable NRF2 activators include bardoxolone and Sulforaphane (an isothiocyanate). Suitable antioxidants include Vitamin C, Vitamin E, alpha lipoic acid, selenium, and carotenoids, such as beta-carotene, lycopene, lutein, and zeaxanthin, and circuminoids (tetrahydrocurcumin, turmeric). Suitable aldosterone antagonists include eplerenone (Inspira) and spironolactone (Aldactone, CaroSpir). Suitable Angiotensin II receptor blockers (ARBs) include Azilsartan (Edarbi), Candesartan (Atacand), Eprosartan, Irbesartan (Avapro), Losartan (Cozaar), Olmesartan (Benicar), Telmisartan (Micardis), Valsartan (Diovan). Suitable ACE Inhibitors include Benazepril (Lotensin), Captopril, Enalapril (Vasotec), Fosinopril, Lisinopril (Prinivil, Zestril), Moexipril, Perindopril (Aceon), Quinapril (Accupril), Ramipril (Altace), or Trandolapril (Mavik). Suitable anti-inflammatory agents include ibuprofen, naproxen and celecoxib. Suitable anti-fibrotic agents include pifrenidone and nintedanib. Suitable vasopressin antagonists include tolvaptan and conivaptan. Suitable SGLT-2 inhibitors include canagliflozin (Invokana), dapagliflozin (Farxiga), empagliflozin (Jardiance), empagliflozin/linagliptin (Glyxambi), empagliflozin/metformin (Synjardy), and dapagliflozin/metformin (Xigduo XR). Suitable immunosuppressive agents can include corticosteroids, Janus kinase inhibitors, Calcineurin inhibitors, mTOR inhibitors, IMDH inhibitors, Biologics, and Monoclonal antibodies. Specific examples of immunosuppressive agents can include prednisone (Deltasone, Orasone), budesonide (Entocort EC), prednisolone (Millipred), tofacitinib (Xeljanz), cyclosporine (Neoral, Sandimmune, SangCya), tacrolimus (Astagraf XL, Envarsus XR, Prograf), azathioprine (Azasan, Imuran), leflunomide (Arava), mycophenolate (CellCept, Myfortic), abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), and daclizumab (Zinbryta). Suitable organ protection agents are preferably renoprotective agents, which can include Frusemide, Dopamine, Theophylline, Mannitol, Calcium channel blockers, α2 Adrenergic receptor agonists, cardiac glycosides, natriuretic peptides, prostaglandins (PGE2, Prostacyclin, Mistoprostol), Nitric oxide synthetase inhibitors (L-NMMA), Catecholamines (Adrenaline, Noradrenaline, Dobutamine, Dopexamine), intravascular volume loading, and other agents including growth factors (IGF1, Epidermal growth factor, Hepatocyte growth factor), Bradykinin, Magnesium, Endothelin-1 antagonists, and low dose endothelin-1. Suitable acute kidney injury treatments include many of the above agents as well as Antiapoptosis/Necrosis Agents (Caspase Inhibitors, Minocycline, Guanosine and Pifithrin-α (p53 Inhibitor), Poly ADP-Ribose Polymerase Inhibitor), Free Radical Scavengers (Deferoxamine), Antisepsis (Ethyl Pyruvate, Activated Protein C, Insulin), Growth Factors (Recombinant Erythropoietin, Hepatocyte Growth Factor), Vasodilators (Carbon Monoxide Release Compounds and Bilirubin, Endothelin Antagonist), anti-inflammatory drugs (e.g., Sphingosine 1 phosphate (S1P) analogs, selective A2AR agonist, Inducible Nitric Oxide Synthase Inhibitors), and other compounds including neutrophil gelatinase-associated lipocalin, IL-6 and C5a antagonists, IL-10, and α-melanocyte-stimulating hormone. Suitable ARBs include Azilsartan (Edarbi), Candesartan (Atacand), Eprosartan, Irbesartan (Avapro), Losartan (Cozaar), Olmesartan (Benicar), Telmisartan (Micardis), Valsartan (Diovan). Suitable ACE Inhibitors include Benazepril (Lotensin), Captopril, Enalapril (Vasotec), Fosinopril, Lisinopril (Prinivil, Zestril), Moexipril, Perindopril (Aceon), Quinapril (Accupril), Ramipril (Altace), or Trandolapril (Mavik).

In one aspect, a patient upon detection of kidney injury in accordance with the above methods may be treated with a combination of iron or an iron complex (e.g., iron sucrose), and a heme protein degradation inhibitor (tin protoporphyrin, SnPP). These treatments are further described in U.S. Pat. No. 9,844,563, entitled Compositions, Kits and Methods to Induce Acquired Cytoresistance Using Stress Protein Inducers, which is incorporated by reference herein in its entirety. The treatment described in the '563 patent allows for protection of an organ before scheduled injury. Where a patent is diagnosed with kidney injury the iron sucrose and SnPP, for example, may be administered to reduce risk of further injury.

In another aspect, the patient upon detection of kidney injury in accordance with the above methods may be treated with a circuminoid (e.g., tetrahydrocurcumin) formulation. These treatments are further described in U.S. Pat. No. 9,375,408, entitled Deuterated or a Non-Deuterated Molecule and Pharmaceutical Formulations. The treatment described in the '408 patent allows one to prevent or slow the progression of kidney injury by administering a tetrahydrocurcumin (THCu) formulation. In one aspect, the THCu is formulated in a liposome.

In yet another aspect, the patient upon detection of kidney injury in accordance with the above methods may be treated with bardoxolone methyl (RTA 402). This compound is described in U.S. Pat. No. 8,455,544, entitled "Synthetic triterpenoids and method of use in the treatment of disease." Bardoxolone methyl is an Antioxidant Inflammation Modulator (AIM) in clinical development for inflammation and cancer-related indications that inhibits immune-mediated inflammation by restoring redox homeostasis in inflamed tissues. It induces the cytoprotective transcription factor Nrf2 and suppresses the activities of the pro-oxidant and pro-inflammatory transcription factors NF-κB and STAT3. In vivo, RTA 402 has demonstrated significant single agent anti-inflammatory activity in several animal models of inflammation such as renal damage in the cisplatin model and acute renal injury in the ischemia-reperfusion model. In addition, significant reductions in serum creatinine have been observed in patients treated with RTA 402.

Another aspect of the p21 biomarker is that its presence naturally increases with aging. Therefore, the patient's age may be taken into consideration in determining the baseline level of p21 above which kidney injury is considered likely. For example a younger patient may be considered as potentially suffering from kidney injury where p21 plasma levels are above 200 pg/ml, whereas an older patient may require p21 plasma levels above 400 pg/ml before kidney injury is considered likely. In either case, p21 levels should rise to levels that dwarf the baseline levels within several hours after kidney injury. For example, levels in the range of greater than 700 pg/ml or 2000 pg/ml can be expected in the case of injury. Alternatively, the baseline level of p21 where kidney injury is considered likely may be set by natural levels observed in older patients.

In another embodiment, the level of intervention could be keyed to the level of p21 biomarker measured. For example, in patients where p21 levels are slightly elevated above the baseline, the intervention may be limited to withdrawing delivery of compounds that are known to be damaging to the kidney, delaying or avoiding procedures that are known to be damaging to the kidney, and modifying diuretic administration. Where further kidney injury is indicated by higher levels of p21, such as levels above 60 pg/ml in the plasma, the treatment may include administration of one or more steroids, ACE inhibitors, NRF2 activators Angiotensin II receptor blockers, antioxidants, aldosterone antagonists, anti-inflammatory, anti-fibrotic, vasopressin antagonists, SGLT-2 inhibitors, immunosuppressive agents, organ protection, or acute kidney injury treatments or could also involve initiating renal replacement therapy.

Figure 8:
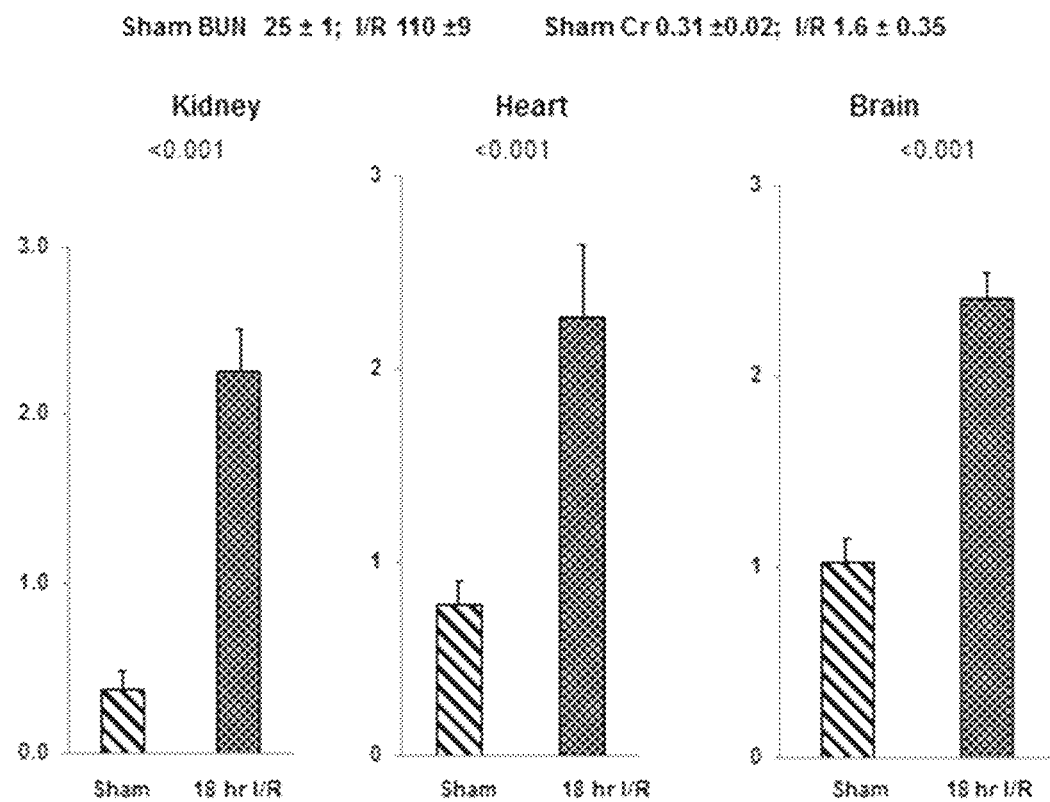
FIG. 8 shows p21 expression in the heart and brain associated with kidney injury.

P21 expression in the heart and brain has been associated with kidney injury as shown in FIG. 8. Renal ischemia was induced by reperfusion or sham surgery, i.e., surgery in the absence of kidney injury. The p21 levels in three organs were measured 18 hours after the reperfusion or sham surgery. Ischemia increased kidney p21 by 6 fold. Surprisingly, however, the renal failure (denoted by the increases in BUN and creatinine (Cr)) also doubled p21 mRNA in heart and brain. So kidney injury evokes p21 gene activation in nonrenal organs.

Proximal tubules were isolated from a mouse kidney and incubated. Through exposure to oxygen deprivation, simulated ischemic injury was induced. A three-fold increase in p21 leakage occurred out of the isolated cells within 30 min and the degree of leakage correlates well with the extent of cell death. It is believed that depleting the cells of ATP made it impossible for the nucleus to retain p21, which presumably is an energy dependent process. The following chart shows increase percentage p21 release after ischemic injury.

| % p21 Release | | |
| --- | --- | --- |
| Date | Control | Hypoxia |
| Jun. 19, 2018 | 0.52 | 0.94 |
| Jun. 19, 2018 | 0.19 | 0.81 |
| Jun. 19, 2018 | 0.40 | 1.44 |
| Jun. 19, 2018 | 0.28 | 1.00 |
| Average | 0.35 | 1.05 |
| Std Error | 0.07 | 0.14 |

These data prove that cell injury causes tubular cell release of p21 from the nucleus of cells into the extracellular (urinary) space. Because p21 is released from the nucleus and makes its way into blood as well as urine is remarkable and distinguishes it from other biomarkers in its ability to indicate damage to the cell nucleus, and presumably its DNA. Moreover, the detectability of p21 in the blood as well as urine enable point of care detection and quantification.

The present invention also includes a urine testing device for measuring levels of p21 in a patient's urine. As noted above, the ability to detect the p21 biomarker in urine makes it particularly advantageous as a biomarker for renal injury, since urine samples are routinely utilized in diagnosis of kidney conditions. The urine testing device includes a test strip which includes two antibodies. Each antibody would be directed to different sites on the p21 protein. One antibody is embedded in the dipstick and binds or captures the p21 in the plasma, serum or urine sample. After exposing the dipstick to the sample for a few minutes, allowing binding of p21, the dipstick would be washed (dunked in saline for a second or two) and then the stick would be put into a solution containing the second antibody which has a detectable readout bound to it (to be defined). The readout molecule (e.g. a fluorescent signal) would then be quantified in a device that can read the fluorescent signal.

The present invention also includes a blood testing device for measuring levels of p21 in a patient's blood. As noted above, the ability to detect the p21 biomarker in blood makes it particularly advantageous as a biomarker for renal injury, since blood samples are routinely utilized in diagnosis of kidney conditions. The device can work with a blood droplet or utilize a pin prick similar to known devices for measuring blood glucose levels for diabetics. The blood testing device includes a test strip which includes two antibodies as described above. Alternatively, the levels of p21 could be done in a clinical lab using nephilometry in situations where a clinical lab is available.

In another aspect, the p21 biomarker may be combined with known AKI biomarkers. Known AKI biomarkers fall into three categories. The first group includes constitutively expressed proximal tubular proteins that are released into urine in response to early AKI. Examples include, lysosomal enzyme N-acetyl β-glucosaminidase (NAG), the cytosolic protein lactate dehydrogenase, or the brush border protein gp330 (previously referred to as the renal tubular epithelial antigen). The second group includes tubule "stress molecules," which respond to injury with increased gene transcription (mRNA elevations), protein translation, and ultimately, protein release into the urinary space. Neutrophil gelatinase-associated lipcalin (NGAL) and KIM-1 are perhaps the best known molecules within this category, although other examples exist (heme oxygenase 1 [HO-1], α-fetoprotein, and haptoglobin). The third category include low molecular mass proteins (e.g., β2-microglobulin, lysozyme, α1-microglobulin, light chains, cystatin c) that are freely filtered by the glomerulus. Because these biomarkers reflect different pathophysiologic pathways, they may be advantageously used in combination with p21 as combination biomarkers.

The p21 protein may also be used as a therapeutic agent to treat various kidney diseases. In this case, human p21 protein may be produced using recombinant technology and administered via intravenous or intramuscular route in order to treat kidney disease. The therapeutically effective dose should be such that upon administration, the patient's level of renal tubular p21 is elevated above the levels naturally present at the time of injury to mitigate its expression. The administration can be made immediately before injury such as in the case of surgery, or may be used to generally raise the p21 levels in the organ where injury is occurring or anticipated. This is because cells make p21 as a protective protein. Recombinant p21 is available, for example, from abcam, 1 Kendall Square, Suite B2304, Cambridge, Mass. 02139-1517 USA.

The p21 protein may also be induced by administration of an agent that causes elevated levels of p21 production in kidney cells. Tenovin-1 is a p21 activator and inducer of cell cycle arrest. Wilking, M. J., Singh, C., Nihal, M., Zhong, W. & Ahmad, N. SIRT1 deacetylase is overexpressed in human melanoma and its small molecule inhibition imparts antiproliferative response via p53 activation. Arch. Biochem. Biophys. 563, 94-100 (2014). The present embodiment involves administering Tenovin-1 in a therapeutically effective amount to a patient in need thereof to treat the patient's kidney disease.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A method of treating a patient at risk for having suffered kidney injury or kidney disease progression comprising:
   (a) performing an assay to determine the level of cyclin-dependent kinase inhibitor p21 in the patient; and
   (b) if the patient exhibits an elevated level of the cyclin-dependent kinase inhibitor p21, treating the patient to reduce the risk of further kidney injury, wherein the treatment comprises one or more of administration of one or more steroids, ACE inhibitors, nuclear factor erythroid 2-related factor 2 (NRF2) activators, Angiotensin II receptor blockers, antioxidants, aldosterone antagonists, anti-inflammatory, anti-fibrotic, vasopressin antagonists, Sodium-glucose Cotransporter-2 (SGLT-2) inhibitors, immunosuppressive agents, organ protection with a combination of iron or iron sucrose and a heme protein degradation inhibitor; or the treatment comprises one or more of initiating renal replacement therapy, withdrawing delivery of compounds that are known to be damaging to the kidney, delaying or avoiding procedures that are known to be damaging to the kidney, and modifying diuretic administration, wherein the cyclin-dependent kinase inhibitor p21 is of SEQ ID NO. 1.

2. The method of claim 1 wherein the assay comprises: (i) obtaining a body fluid sample from the patient, (ii) contacting all or a portion of the body fluid sample with a binding reagent which specifically binds for detection of the cyclin-dependent kinase inhibitor p21, and determining an assay result indicative of binding of the cyclin-dependent kinase inhibitor p21 to the binding reagent to provide one or more assay results.

3. The method of claim 1 wherein the treatment comprises administration of one or more steroids, cellular senescence blocking agents, ACE inhibitors, NRF2 activators, Angiotensin II receptor blockers, anti-inflammatory, anti-fibrotic, vasopressin antagonists, SGLT-2 inhibitors, immunosuppressive agents, organ protection with a combination of iron or iron sucrose and a heme protein degradation inhibitor.

4. The method of claim 1, wherein the patient is treated with a combination of iron or an iron complex, and a heme protein degradation inhibitor.

5. The method of claim 1, wherein the patient is treated with a combination of iron sucrose and tin protoporphyrin.

6. The method of claim 1, wherein the patient is treated with a circuminoid formulation.

7. The method of claim 1, wherein the patient is treated with bardoxolone methyl.

8. A method of determining the risk of progression of acute or chronic kidney disease and tissue senescence comprising:
  (a) performing an assay to determine the level of organ senescence as shown by the level of serum, urine, or plasma the cyclin-dependent kinase inhibitor p21 levels in the patient; and
  (b) if the patient exhibits an elevated level of the cyclin-dependent kinase inhibitor p21, administer a dosage of a drug known to treat senescence in the patient, wherein the cyclin-dependent kinase inhibitor p21 is of SEQ ID NO. 1.

9. The method of claim 8, wherein the assay comprises: (i) obtaining a body fluid sample from the patient, (ii) contacting all or a portion of the body fluid sample with a binding reagent which specifically binds for detection of the cyclin-dependent kinase inhibitor p21, and determining an assay result indicative of binding of the cyclin-dependent kinase inhibitor p21 to the binding reagent to provide one or more assay results.

10. The method of claim 8, wherein the dosage of the drug known to treat senescence is increased upon determination that the level of the cyclin-dependent kinase inhibitor p21 is increased.

11. A method of treating a patient determined to be at risk for future kidney injury comprising:
  (a) performing an assay to determine the level of the cyclin-dependent kinase inhibitor p21 in the patient;
  (b) performing an assay to determine the level of urinary albumin in the patient; and
  (c) if the patient exhibits elevated levels of the cyclin-dependent kinase inhibitor p21 and albumin, treating the patient to reduce the risk of further kidney injury, wherein the treatment comprises one or more of administration of one or more steroids, ACE inhibitors, NRF2 activators, antioxidants, aldosterone antagonists, anti-inflammatory, anti-fibrotic, vasopressin antagonists, SGLT-2 inhibitors, immunosuppressive agents, organ protection with a combination of iron or iron sucrose and a heme protein degradation inhibitor; or the treatment comprises one or more of initiating renal replacement therapy, withdrawing delivery of compounds that are known to be damaging to the kidney, delaying or avoiding procedures that are known to be damaging to the kidney, and modifying diuretic administration, wherein the cyclin-dependent kinase inhibitor p21 is of SEQ ID NO. 1.

12. The method of claim 11, wherein the patient is treated with a combination of iron or an iron complex, and a heme protein degradation inhibitor.

13. The method of claim 11, wherein the cyclin-dependent kinase inhibitor p21 is recombinant human cyclin-dependent kinase inhibitor p21.

* * * * *